(12) United States Patent
Baril et al.

(10) Patent No.: US 11,751,908 B2
(45) Date of Patent: Sep. 12, 2023

(54) SEAL ASSEMBLY FOR SURGICAL ACCESS ASSEMBLIES

(71) Applicant: Covidien LP, Mansfield, MA (US)

(72) Inventors: Jacob C. Baril, Norwalk, CT (US); Garrett P. Ebersole, Hamden, CT (US); Justin Thomas, New Haven, CT (US); Roy J. Pilletere, North Haven, CT (US); Nicolette R. LaPierre, Windsor Locks, CT (US)

(73) Assignee: Covidien LP, Mansfield, MA (US)

( * ) Notice: Subject to any disclaimer, the term of this patent is extended or adjusted under 35 U.S.C. 154(b) by 239 days.

(21) Appl. No.: 16/906,331

(22) Filed: Jun. 19, 2020

(65) Prior Publication Data

US 2021/0393290 A1 Dec. 23, 2021

(51) Int. Cl.
*A61B 17/34* (2006.01)
*A61B 17/00* (2006.01)

(52) U.S. Cl.
CPC ...... *A61B 17/3462* (2013.01); *A61B 17/3423* (2013.01); *A61B 17/3498* (2013.01); *A61B 2017/00862* (2013.01); *A61B 2017/3425* (2013.01); *A61B 2017/3486* (2013.01)

(58) Field of Classification Search
CPC .............. A61B 17/3462–2017/3466; A61B 17/3423–2017/3427; A61B 17/3498; A61B 2017/00862; A61B 17/3439

See application file for complete search history.

(56) References Cited

U.S. PATENT DOCUMENTS

| 3,402,710 A | 9/1968 | Paleschuck |
| 3,495,586 A | 2/1970 | Regenbogen |
| 4,016,884 A | 4/1977 | Kwan-Gett |

(Continued)

FOREIGN PATENT DOCUMENTS

| CA | 2702419 A1 | 11/2010 |
| EP | 0226026 A2 | 6/1987 |

(Continued)

OTHER PUBLICATIONS

Extended European Search Report issued in corresponding European Application No. 21180128.7 dated Oct. 22, 2021, 10 pages.

(Continued)

*Primary Examiner* — Darwin P Erezo
*Assistant Examiner* — Brigid K Byrd
(74) *Attorney, Agent, or Firm* — Carter, DeLuca & Farrell LLP

(57) ABSTRACT

A surgical access assembly includes an instrument valve housing defining a cavity, and a seal assembly disposed within the cavity of the instrument valve housing. The seal assembly includes a flange seal member and a centering mechanism. The flange seal member includes an annular member, a flange portion extending from the annular member, and a seal portion supported by the annular member and defining an opening dimensioned to receive a surgical instrument in a sealing relation. The flange portion includes first and second arcuate portions adjustably engaging the instrument valve housing in a sealing relation. The first and second arcuate portions have a parabolic profile. The centering mechanism maintains the seal assembly centered within the cavity of the instrument valve housing.

18 Claims, 7 Drawing Sheets

(56) References Cited

U.S. PATENT DOCUMENTS

| | | | |
|---|---|---|---|
| 4,112,932 | A | 9/1978 | Chiulli |
| 4,183,357 | A | 1/1980 | Bentley et al. |
| 4,356,826 | A | 11/1982 | Kubota |
| 4,402,683 | A | 9/1983 | Kopman |
| 4,653,476 | A | 3/1987 | Bonnet |
| 4,737,148 | A | 4/1988 | Blake |
| 4,863,430 | A | 9/1989 | Klyce et al. |
| 4,863,438 | A | 9/1989 | Gauderer et al. |
| 4,984,564 | A | 1/1991 | Yuen |
| 5,002,557 | A | 3/1991 | Hasson |
| 5,073,169 | A | 12/1991 | Raiken |
| 5,082,005 | A | 1/1992 | Kaldany |
| 5,122,122 | A | 6/1992 | Allgood |
| 5,159,921 | A | 11/1992 | Hoover |
| 5,176,697 | A | 1/1993 | Hasson et al. |
| 5,183,471 | A | 2/1993 | Wilk |
| 5,192,301 | A | 3/1993 | Kamiya et al. |
| 5,209,741 | A | 5/1993 | Spaeth |
| 5,209,754 | A | 5/1993 | Ahluwalia |
| 5,217,466 | A | 6/1993 | Hasson |
| 5,242,409 | A | 9/1993 | Buelna |
| 5,242,415 | A | 9/1993 | Kantrowitz et al. |
| 5,257,973 | A | 11/1993 | Villasuso |
| 5,257,975 | A | 11/1993 | Foshee |
| 5,269,772 | A | 12/1993 | Wilk |
| 5,290,249 | A | 3/1994 | Foster et al. |
| 5,312,391 | A | 5/1994 | Wilk |
| 5,312,417 | A | 5/1994 | Wilk |
| 5,314,417 | A | 5/1994 | Stephens et al. |
| 5,318,516 | A | 6/1994 | Cosmescu |
| 5,330,486 | A | 7/1994 | Wilk |
| 5,334,143 | A | 8/1994 | Carroll |
| 5,336,169 | A | 8/1994 | Divilio et al. |
| 5,336,203 | A | 8/1994 | Goldhardt et al. |
| 5,337,937 | A | 8/1994 | Remiszewski et al. |
| 5,345,927 | A | 9/1994 | Bonutti |
| 5,360,417 | A | 11/1994 | Gravener et al. |
| 5,366,478 | A | 11/1994 | Brinkerhoff et al. |
| 5,375,588 | A | 12/1994 | Yoon |
| 5,378,588 | A | 1/1995 | Tsuchiya |
| 5,391,156 | A | 2/1995 | Hildwein et al. |
| 5,394,863 | A | 3/1995 | Sanford et al. |
| 5,395,367 | A | 3/1995 | Wilk |
| 5,437,683 | A | 8/1995 | Neumann et al. |
| 5,445,615 | A | 8/1995 | Yoon |
| 5,451,222 | A | 9/1995 | De Maagd et al. |
| 5,460,170 | A | 10/1995 | Hammerslag |
| 5,464,409 | A | 11/1995 | Mohajer |
| 5,480,410 | A | 1/1996 | Cuschieri et al. |
| 5,490,843 | A | 2/1996 | Hildwein et al. |
| 5,507,758 | A | 4/1996 | Thomason et al. |
| 5,511,564 | A | 4/1996 | Wilk |
| 5,514,133 | A | 5/1996 | Golub et al. |
| 5,514,153 | A | 5/1996 | Bonutti |
| 5,520,698 | A | 5/1996 | Koh |
| 5,522,791 | A | 6/1996 | Leyva |
| 5,524,644 | A | 6/1996 | Crook |
| 5,540,648 | A | 7/1996 | Yoon |
| 5,545,150 | A | 8/1996 | Danks et al. |
| 5,545,179 | A | 8/1996 | Williamson, IV |
| 5,556,385 | A | 9/1996 | Andersen |
| 5,569,159 | A | 10/1996 | Anderson et al. |
| 5,577,993 | A | 11/1996 | Zhu et al. |
| 5,601,581 | A | 2/1997 | Fogarty et al. |
| 5,624,399 | A | 4/1997 | Ackerman |
| 5,634,911 | A | 6/1997 | Hermann et al. |
| 5,634,937 | A | 6/1997 | Mollenauer et al. |
| 5,643,285 | A | 7/1997 | Rowden et al. |
| 5,649,550 | A | 7/1997 | Crook |
| 5,651,771 | A | 7/1997 | Tangherlini et al. |
| 5,653,705 | A | 8/1997 | de la Torre et al. |
| 5,656,013 | A | 8/1997 | Yoon |
| 5,672,168 | A | 9/1997 | de la Torre et al. |
| 5,683,378 | A | 11/1997 | Christy |
| 5,685,857 | A | 11/1997 | Negus et al. |
| 5,697,946 | A | 12/1997 | Hopper et al. |
| 5,709,675 | A | 1/1998 | Williams |
| 5,713,858 | A | 2/1998 | Heruth et al. |
| 5,713,869 | A | 2/1998 | Morejon |
| 5,722,962 | A | 3/1998 | Garcia |
| 5,728,103 | A | 3/1998 | Picha et al. |
| 5,730,748 | A | 3/1998 | Fogarty et al. |
| 5,735,791 | A | 4/1998 | Alexander, Jr. et al. |
| 5,741,298 | A | 4/1998 | MacLeod |
| 5,752,938 | A * | 5/1998 | Flatland ............ A61B 17/3498 604/167.01 |
| 5,752,970 | A | 5/1998 | Yoon |
| 5,782,817 | A | 7/1998 | Franzel et al. |
| 5,795,290 | A | 8/1998 | Bridges |
| 5,803,921 | A | 9/1998 | Bonadio |
| 5,810,712 | A | 9/1998 | Dunn |
| 5,813,409 | A | 9/1998 | Leahy et al. |
| 5,830,191 | A | 11/1998 | Hildwein et al. |
| 5,836,871 | A | 11/1998 | Wallace et al. |
| 5,836,913 | A | 11/1998 | Orth et al. |
| 5,840,077 | A | 11/1998 | Rowden et al. |
| 5,842,971 | A | 12/1998 | Yoon |
| 5,848,992 | A | 12/1998 | Hart et al. |
| 5,853,417 | A | 12/1998 | Fogarty et al. |
| 5,857,461 | A | 1/1999 | Levitsky et al. |
| 5,865,817 | A | 2/1999 | Moenning et al. |
| 5,871,474 | A | 2/1999 | Hermann et al. |
| 5,876,413 | A | 3/1999 | Fogarty et al. |
| 5,894,843 | A | 4/1999 | Benetti et al. |
| 5,899,208 | A | 5/1999 | Bonadio |
| 5,899,913 | A | 5/1999 | Fogarty et al. |
| 5,904,703 | A | 5/1999 | Gilson |
| 5,906,577 | A | 5/1999 | Beane et al. |
| 5,914,415 | A | 6/1999 | Tago |
| 5,916,198 | A | 6/1999 | Dillow |
| 5,941,898 | A | 8/1999 | Moenning et al. |
| 5,951,588 | A | 9/1999 | Moenning |
| 5,957,913 | A | 9/1999 | de la Torre et al. |
| 5,964,781 | A | 10/1999 | Mollenauer et al. |
| 5,976,174 | A | 11/1999 | Ruiz |
| 5,997,515 | A | 12/1999 | de la Torre et al. |
| 6,017,355 | A | 1/2000 | Hessel et al. |
| 6,018,094 | A | 1/2000 | Fox |
| 6,024,736 | A | 2/2000 | de la Torre et al. |
| 6,030,402 | A | 2/2000 | Thompson et al. |
| 6,033,426 | A | 3/2000 | Kaji |
| 6,033,428 | A | 3/2000 | Sardella |
| 6,042,573 | A | 3/2000 | Lucey |
| 6,048,309 | A | 4/2000 | Flom et al. |
| 6,059,816 | A | 5/2000 | Moenning |
| 6,068,639 | A | 5/2000 | Fogarty et al. |
| 6,077,288 | A | 6/2000 | Shimomura et al. |
| 6,086,603 | A | 7/2000 | Termin et al. |
| 6,099,506 | A | 8/2000 | Macoviak et al. |
| 6,110,154 | A | 8/2000 | Shimomura et al. |
| 6,142,936 | A | 11/2000 | Beane et al. |
| 6,156,006 | A | 12/2000 | Brosens et al. |
| 6,162,196 | A | 12/2000 | Hart et al. |
| 6,171,282 | B1 | 1/2001 | Ragsdale |
| 6,197,002 | B1 | 3/2001 | Peterson |
| 6,217,555 | B1 | 4/2001 | Hart et al. |
| 6,228,063 | B1 | 5/2001 | Aboul-Hosn |
| 6,234,958 | B1 | 5/2001 | Snoke et al. |
| 6,238,373 | B1 | 5/2001 | de la Torre et al. |
| 6,241,768 | B1 | 6/2001 | Agarwal et al. |
| 6,251,119 | B1 | 6/2001 | Addis |
| 6,254,534 | B1 | 7/2001 | Butler et al. |
| 6,264,604 | B1 | 7/2001 | Kieturakis et al. |
| 6,276,661 | B1 | 8/2001 | Laird |
| 6,293,952 | B1 | 9/2001 | Brosens et al. |
| 6,315,770 | B1 | 11/2001 | de la Torre et al. |
| 6,319,246 | B1 | 11/2001 | de la Torre et al. |
| 6,328,720 | B1 | 12/2001 | McNally et al. |
| 6,329,637 | B1 | 12/2001 | Hembree et al. |
| 6,371,968 | B1 | 4/2002 | Kogasaka et al. |
| 6,382,211 | B1 | 5/2002 | Crook |
| 6,423,036 | B1 | 7/2002 | Van Huizen |
| 6,440,061 | B1 | 8/2002 | Wenner et al. |
| 6,440,063 | B1 | 8/2002 | Beane et al. |

(56) References Cited

U.S. PATENT DOCUMENTS

| | | |
|---|---|---|
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,448 B2 | 11/2007 | Criscuolo et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |

(56) References Cited

U.S. PATENT DOCUMENTS

| | | |
|---|---|---|
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 10,568,660 B2 | 2/2020 | Zhou |
| 10,653,449 B2 | 5/2020 | Main et al. |
| 2001/0037053 A1 | 11/2001 | Bonadio et al. |
| 2002/0055714 A1 | 5/2002 | Rothschild |
| 2002/0072713 A1* | 6/2002 | Almond ............ A61B 17/3462 604/167.05 |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0059934 A1* | 3/2005 | Wenchell ............ A61B 18/1445 604/167.01 |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251560 A1 | 10/2011 | Albrecht et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |

(56) References Cited

U.S. PATENT DOCUMENTS

| | | |
|---|---|---|
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0025477 A1 | 1/2015 | Evans |
| 2015/0031958 A1* | 1/2015 | Kleyman ........... A61B 17/3423 600/204 |
| 2015/0223833 A1 | 8/2015 | Coffeen et al. |
| 2017/0095269 A1* | 4/2017 | Reid ................... A61B 17/3423 |
| 2019/0059938 A1* | 2/2019 | Holsten ............... A61B 17/3462 |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 1994896 A1 | 11/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2314334 A1 | 4/2011 |
| EP | 2343019 | 7/2011 |
| EP | 2900153 B1 | 5/2018 |
| EP | 2958502 B1 | 9/2020 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2014116889 A1 | 7/2014 |
| WO | 2016110720 A1 | 7/2016 |
| WO | 2016186905 A1 | 11/2016 |

OTHER PUBLICATIONS

European Search Report dated Jul. 3, 2020, issued in EP Appln. No. 20156174, 8 pages.
European Office Action dated Sep. 20, 2022, issued in corresponding EP Application No. 21180128, 5 pages.

* cited by examiner

SEAL ASSEMBLY FOR SURGICAL ACCESS ASSEMBLIES

FIELD

The present disclosure relates to surgical access assemblies for minimally invasive surgery and, more particularly, to a seal assembly for use with the surgical access assemblies.

BACKGROUND

In order to facilitate minimally invasive surgery, a working space must be created in the desired surgical space. An insufflation gas, typically $CO_2$, is introduced into the abdomen of the patient to create an inflated state called pneumoperitoneum. Surgical access assemblies are utilized to allow the introduction of surgical instrumentation and endoscopes (or other visualization tools). These surgical access assemblies maintain the pressure of the pneumoperitoneum, as they have one or more seals. Typically, a "zero-seal" in the surgical access assemblies seals a surgical access assembly in the absence of a surgical instrument therein, and an instrument seal seals around a surgical instrument that is inserted through the surgical access assembly.

Surgical procedures require a robust seal capable of adjusting to manipulation of surgical instrumentation extending through the surgical access assemblies without compromising seal integrity. Therefore, it would be beneficial to have a surgical access assembly with improved seal capability and durability.

SUMMARY

As used herein, the term "distal" refers to that portion of the instrument, or component thereof which is farther from the user while the term "proximal" refers to that portion of the instrument or component thereof which is closer to the user. In addition, the terms parallel and perpendicular are understood to include relative configurations that are substantially parallel and substantially perpendicular up to about + or −10 degrees from true parallel and true perpendicular. As used herein, the term "about" means that the numerical value is approximate and small variations would not significantly affect the practice of the disclosure. Further, to the extent consistent, any or all of the aspects detailed herein may be used in conjunction with any or all of the other aspects detailed herein.

In accordance with the disclosure, a surgical access assembly includes an instrument valve housing defining a cavity, and a seal assembly disposed within the cavity of the instrument valve housing. The seal assembly includes a flange seal member and a centering mechanism. The flange seal member includes an annular member, a flange portion extending from the annular member, and a seal portion supported by the annular member and defining an opening dimensioned to receive a surgical instrument in a sealing relation. The flange portion includes first and second arcuate portions adjustably engaging the instrument valve housing in a sealing relation. The first and second arcuate portions have a parabolic profile. The centering mechanism maintains the seal assembly centered within the cavity of the instrument valve housing.

In an aspect, the flange seal member may be integrally formed as a single construct.

In another aspect, the first arcuate portion may extend radially inwards from the annular member.

In yet another aspect, the second arcuate portion may extend radially outwards from the annular member.

In an aspect, the flange portion may be formed of a resilient or elastic material.

In another aspect, the first and second arcuate portions may define a recess therebetween.

In yet another aspect, at least one of the first or second arcuate portions may be configured to contact a surface of the instrument valve assembly.

In still yet another aspect, the centering mechanism may include an annular base and a plurality of spokes extending radially from the annular base.

In still yet another aspect, the annular base of the centering mechanism may be disposed about the annular member of the flange seal member.

In an aspect, the seal assembly may further include a retaining frame assembly including first and second frames securing the flange seal member and the centering mechanism to move as a single construct.

In another aspect, the first frame may include a plurality of pins extending through the flange seal member and into a circular groove defined in the second frame.

In accordance with another aspect of the disclosure, a surgical access assembly includes a cannula, an instrument valve housing detachably coupled to the cannula, and a seal assembly adjustably supported within the instrument valve housing. The seal assembly includes a flange seal member and a centering mechanism. The flange seal member includes an annular member, a flange portion extending from the annular member, and a seal portion extending radially inwards from the annular member and defining an opening dimensioned to receive a surgical instrument in a sealing relation. The flange portion is spaced apart from the seal portion. The flange portion includes first and second arcuate portions extending in opposite directions from the annular member to provide a seal against the instrument valve housing. The centering mechanism is configured to bias the seal assembly towards a generally centered position within the instrument valve housing.

In an aspect, at least a portion of the seal portion of the flange seal member may be in a superposed relation with the first arcuate portion of the flange portion.

In another aspect, the first and second arcuate portions of the flange portion may be symmetric.

In yet another aspect, the first and second arcuate portions may define a parabolic profile.

In still yet another aspect, the first and second arcuate portions may be configured for respective planar contacts with the instrument valve housing.

In an aspect, the first and second arcuate portions of the flange portion may be configured to engage a first surface orthogonal to a longitudinal axis defined by the cannula.

In another aspect, the second arcuate portion of the flange portion may be configured to engage a second surface orthogonal to the first surface in a sealing relation.

In another aspect, the flange seal member may be monolithically formed.

BRIEF DESCRIPTION OF DRAWINGS

Various aspects and features of the present disclosure are described hereinbelow with reference to the drawings wherein like numerals designate identical or corresponding elements in each of the several views.

DETAILED DESCRIPTION

Figure 1:
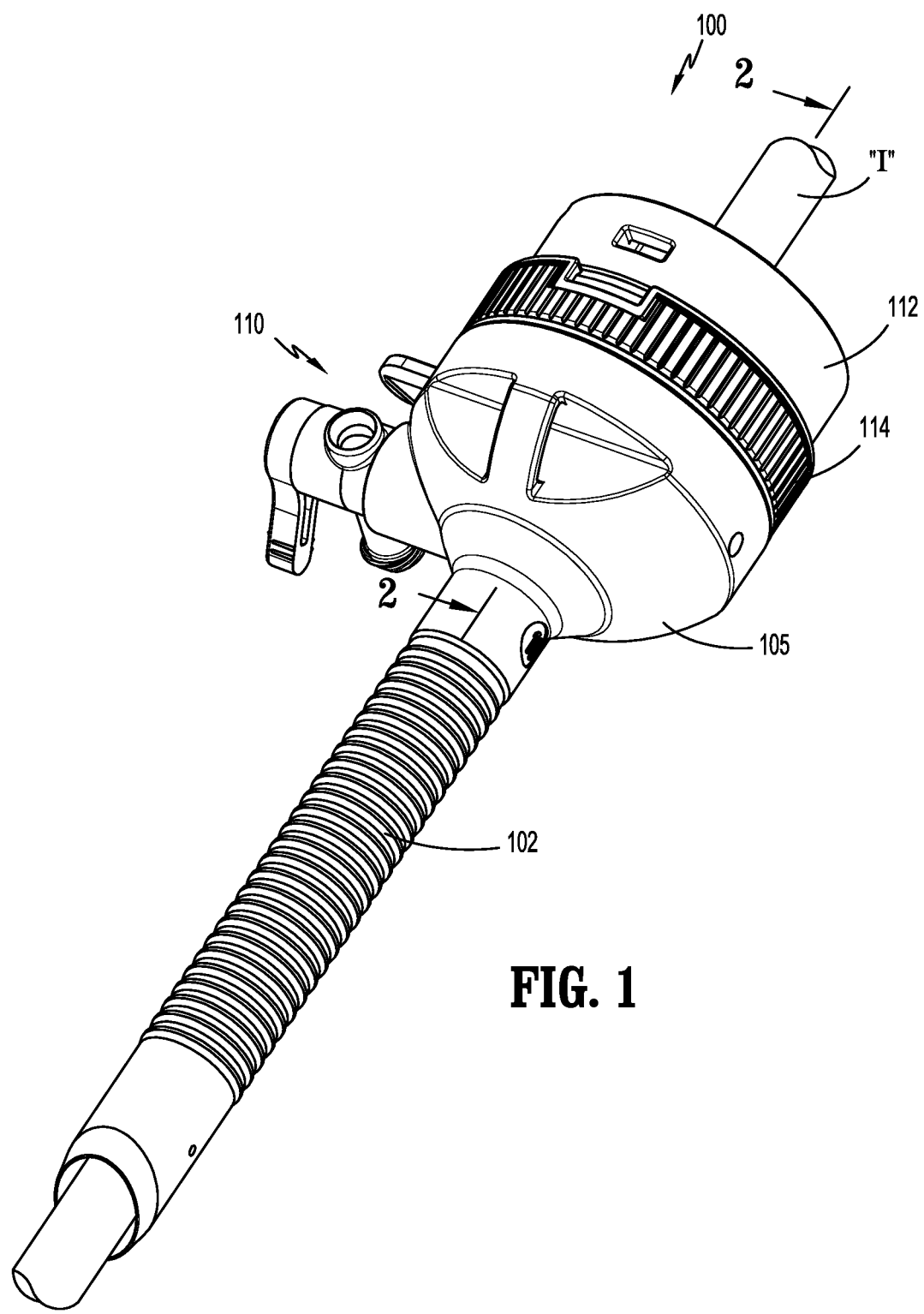
FIG. 1 is a perspective view of a surgical access assembly in accordance with the present disclosure.

The surgical access assembly disclosed herein is described in detail with reference to the drawings, in which like reference numerals designate identical or corresponding elements in each of the several views.

Figure 2:
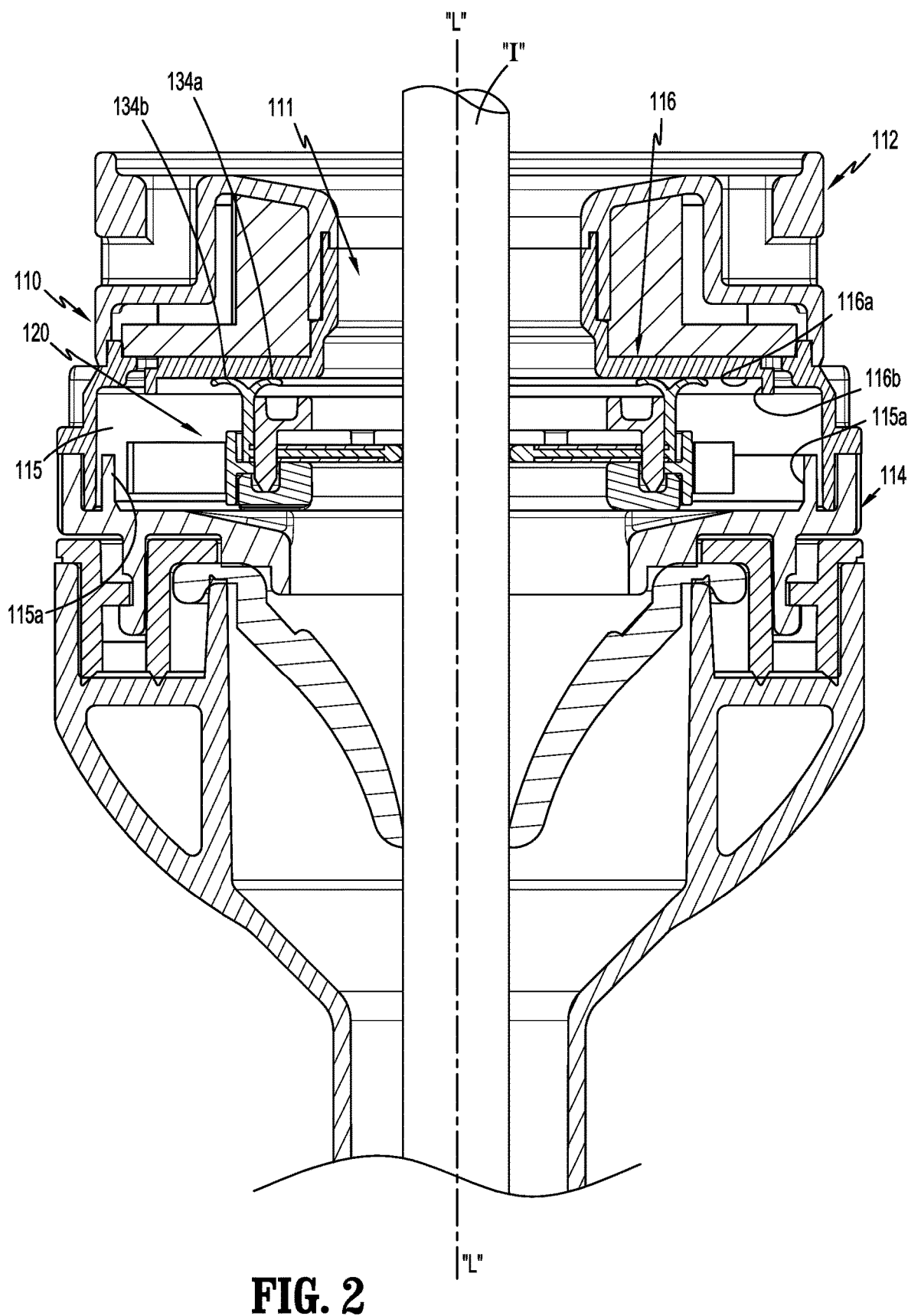
FIG. 2 a side cross-sectional view of a proximal region of the surgical access assembly of FIG. 1 taken along section line 2-2 of FIG. 1.

With initial reference to FIGS. 1 and 2, a surgical access assembly in the form of a cannula assembly in accordance with the present disclosure is shown generally as a cannula assembly 100. The cannula assembly 100 may be utilized during minimally invasive surgery, e.g., laparoscopic surgery, to provide sealed access of surgical instruments into an insufflated body cavity, such as the abdominal cavity. The cannula assembly 100 includes a cannula 102 and an instrument valve housing 110 detachably secured to a base portion 105 of the cannula 102. The instrument valve housing 110 includes an upper housing section 112, a lower housing section 114, and an inner housing section 116. The base portion 105 may be secured with or integrally formed with the cannula 102. The upper, lower, and inner housing sections 112, 114, 116 are coupled to the base portion 105 and are configured to adjustably support a seal assembly 120. In particular, the inner housing section 116 is secured between the upper and lower housing sections 112, 114, and the seal assembly 120 is received between the inner and lower housing sections 116, 114. The upper and lower housing sections 112, 114 of the instrument valve housing 110 may be selectively attachable to, and detachable from, the inner housing section 116. The lower housing section 114 may be releasably or permanently attached to the base portion 105. Either or both of the upper and lower housing sections 112, 114 of the instrument valve housing 110 may include knurls, indentations, tabs, or be otherwise configured to facilitate engagement by a clinician.

The cannula assembly 100 may be configured for use with an obturator (not shown) inserted through the instrument valve housing 110 and the cannula 102. The obturator may have a blunt distal end, or a bladed or non-bladed penetrating distal end. The obturator may be used to incise the abdominal wall so that the cannula assembly 100 may be introduced into the abdomen. The handle of the obturator may engage or selectively lock into the instrument valve housing 110 of the cannula assembly 100. For a detailed description of the structure and function of exemplary obturators and cannulas, reference may be made to commonly owned International Patent Publication No. WO 2016/186905, the entire disclosure of which is hereby incorporated by reference herein.

In addition, the cannula assembly 100 may also include features for securement with a patient. For example, a distal end of the cannula 102 may support a balloon anchor or another expandable member that engages the abdomen from the interior side. A feature on the opposite side of the abdominal wall may be used to further stabilize the cannula assembly 100, such as adhesive tabs or adjustable foam collars. For a detailed description of such features on a cannula assembly, reference may be made to commonly owned U.S. Pat. No. 7,300,448, the entire disclosure of which is hereby incorporated by reference herein.

With particular reference to FIG. 2, the instrument valve housing 110 defines a longitudinal passage 111 for receipt of a surgical instrument "I". In addition, the instrument valve housing 110 defines a cavity 115 configured to adjustably support the seal assembly 120 therein. The seal assembly 120 is supported within the instrument valve housing 110 to provide sealed passage of the surgical instrument "I" through the access assembly 100.

Figure 3:
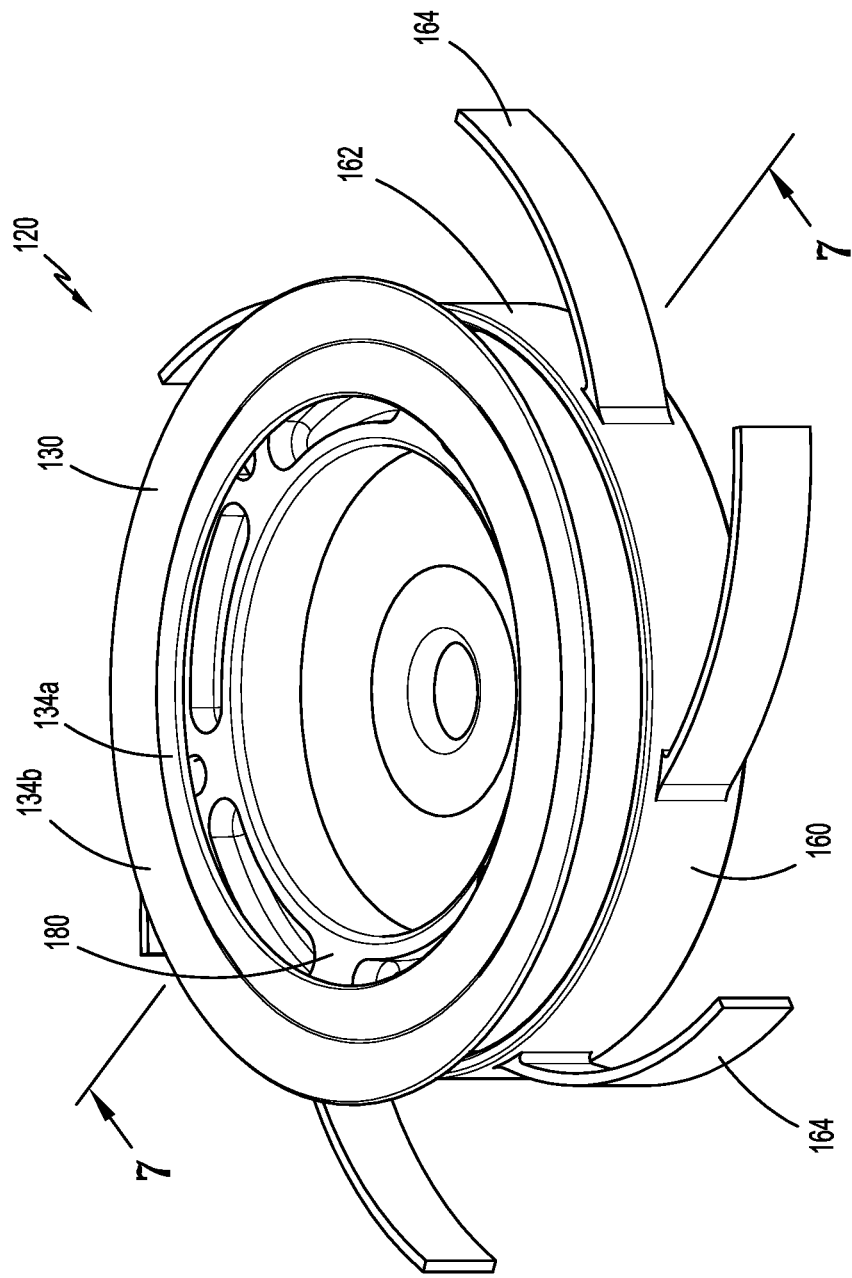
FIG. 3 is a perspective view of a seal assembly of the surgical access assembly of FIG. 1.
Figure 4:
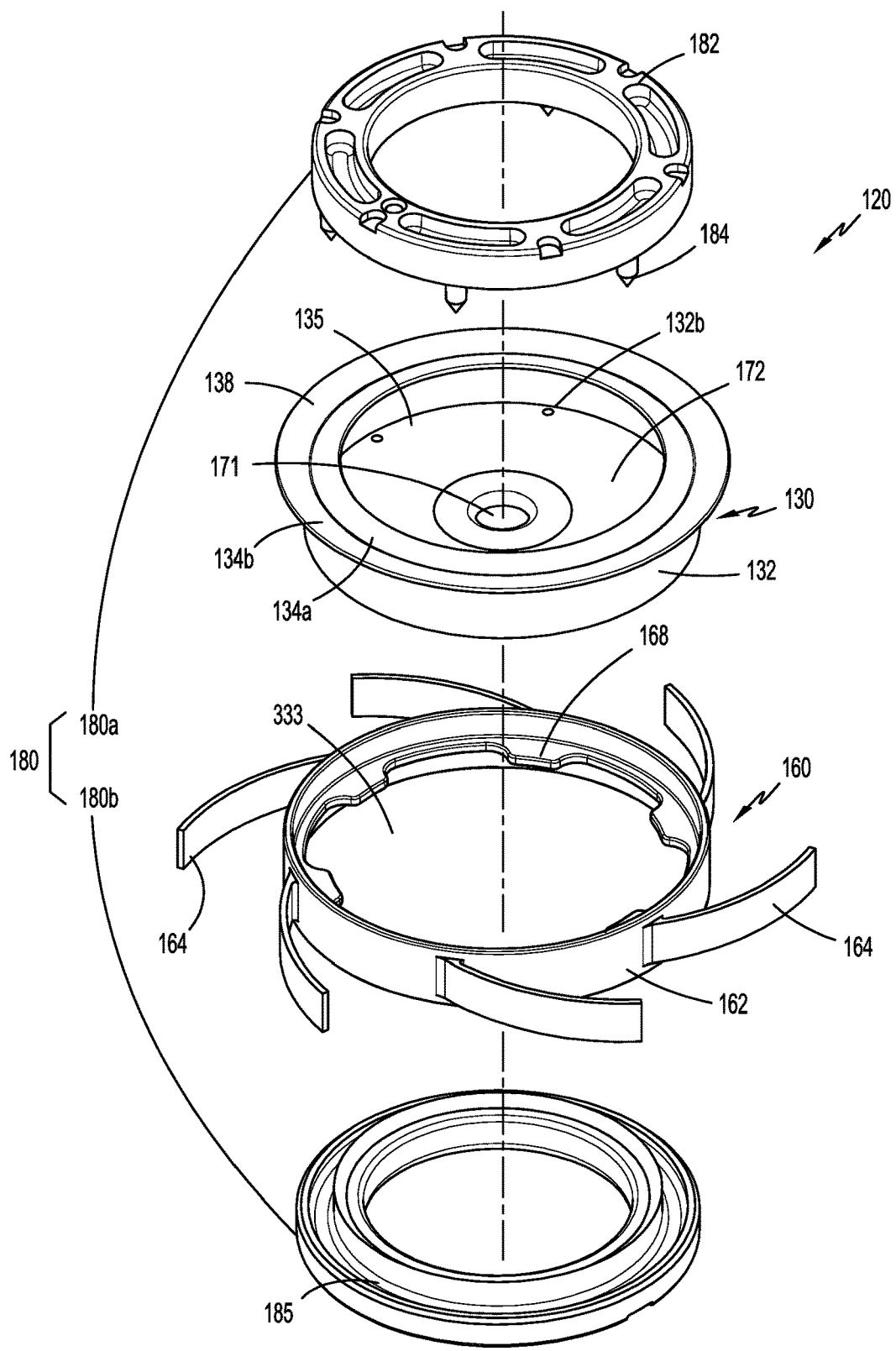
FIG. 4 is an exploded perspective view of the seal assembly of FIG. 3 with parts separated.

With reference now to FIGS. 3 and 4, the seal assembly 120 in accordance with the present disclosure includes a flange seal member 130, a centering mechanism 160, and a retainer frame assembly 180. The flange seal assembly 130 provides sealed passage of the surgical instrument "I" (FIG. 2) through the instrument valve housing 110 (FIG. 2). The centering mechanism 160 enables radial movement of the flange seal member 130 relative to the instrument valve housing 110 when the surgical instrument "I" is received through the seal assembly 120, and returns the seal assembly 120 to a generally centered position once the surgical instrument "I" is withdrawn from within the instrument valve housing 110. The retainer frame assembly 180 maintains the centering mechanism 160 and the flange seal assembly 130 in registration with each other.

The flange seal member 130 includes an annular member 132, a flange portion 138, and a seal portion 172 extending radially inward from the annular member 132. The seal portion 172 is formed of an elastic material such as, e.g., rubber, and defines a central opening 171 and a plurality of bores 132b circumferentially defined about the central opening 171. The central opening 171 of the seal portion 172 is configured to receive the surgical instrument "I" therethrough, and the plurality of bores 132b is configured to receive respective pins 184 of the first frame 180a of the retainer frame assembly 180. The seal portion 172 is configured to direct the surgical instrument "I" through the central opening 171 in the seal portion 172. The flange portion 138 extends from the annular member 132 such that the flange seal member 130 defines a recess 135 configured to support a first frame 180a of the retainer frame assembly 180 thereon. The annular member 132 and the flange portion 138 may be integrally formed as a single construct. In an aspect, at least the flange portion 138 and the seal portion 172 may be formed of a resilient or elastic material such as, e.g., rubber. In an aspect, the flange seal member 130 may be monolithically formed.

Figure 5:
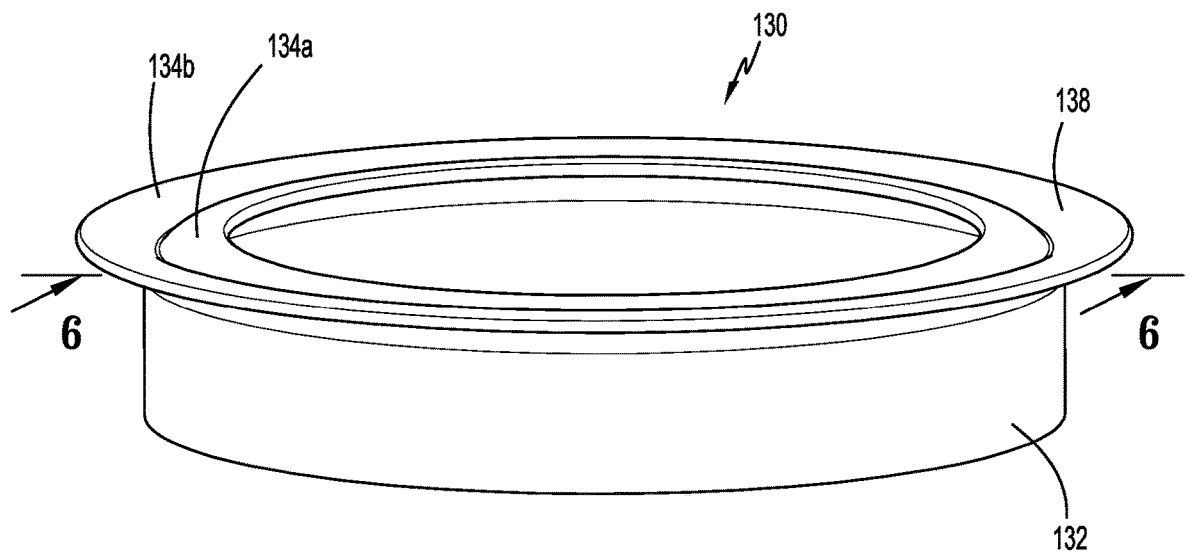
FIG. 5 is a perspective view of a flange seal member of the seal assembly of FIG. 4.
Figure 6:
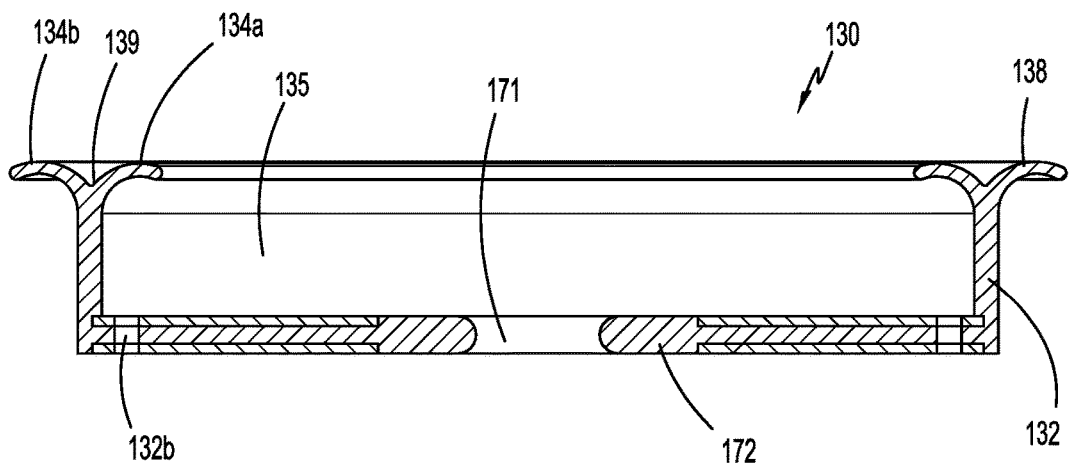
FIG. 6 is a cross-sectional view of the flange seal member of FIG. 5 taken along section line 6-6 of FIG. 5.

With reference to FIGS. 5 and 6, the flange portion 138 of the flange seal member 130 includes a first arcuate portion 134a extending radially inwards from the annular member 132 and a second arcuate portion 134b extending radially outwards from the annular member 132. The first and second arcuate portions 134a, 134b may be symmetrical. The first and second arcuate portions 134a, 134b are configured to engage the inner housing segment 116 in a sealing relation. For example, the first and second arcuate portions 134a, 134b may be in, e.g., surface contact, with a distal surface 116a (FIG. 2) of the inner housing segment 116. For example, the distal surface 116a of the inner housing section 116 of the instrument valve housing 110 may be orthogonal to a longitudinal axis "L-L" (FIG. 2) defined by the longitudinal passage 111 of the instrument valve housing 110.

Further, the first and second arcuate portions 134a, 134b may have, e.g., a parabolic, profile. The flange portion 138 may define a recess 139 between the first and second arcuate portions 134a, 134b. For example, the flange portion 138 and the annular member 132 may have a cross-section having a Y-shaped profile. Such a configuration ensures at least two points of contact against the distal surface 116a (FIG. 2) of the inner housing segment 116 of the instrument valve housing 110. Under such a configuration, the first and second arcuate portions 134a, 134b are configured to adjustably engage the distal surface 116a of the inner housing segment 116 (FIG. 2) of the instrument valve housing 110 in a sealing relation and maintain such contact during insertion and movement of the surgical instrument "I" in the longitudinal passage 111 (FIG. 2). This arrangement minimizes buckling or bending during movement of the seal, which may result in a loss of sealing contact with the surgical instrument "I" and/or the instrument valve housing. In contrast, the flange seal member 130 engages the inner housing segment 116 of the instrument valve housing 110 in a sealing relation during movement of the seal assembly 120 within the cavity 115. In particular, the first and second arcuate portions 134a, 134b of the flange seal member 130 adjustably engages the inner housing segment 116 of the instrument valve housing 110 to enable sealing contact during, e.g., radial, movement in the cavity 115.

Figure 7:
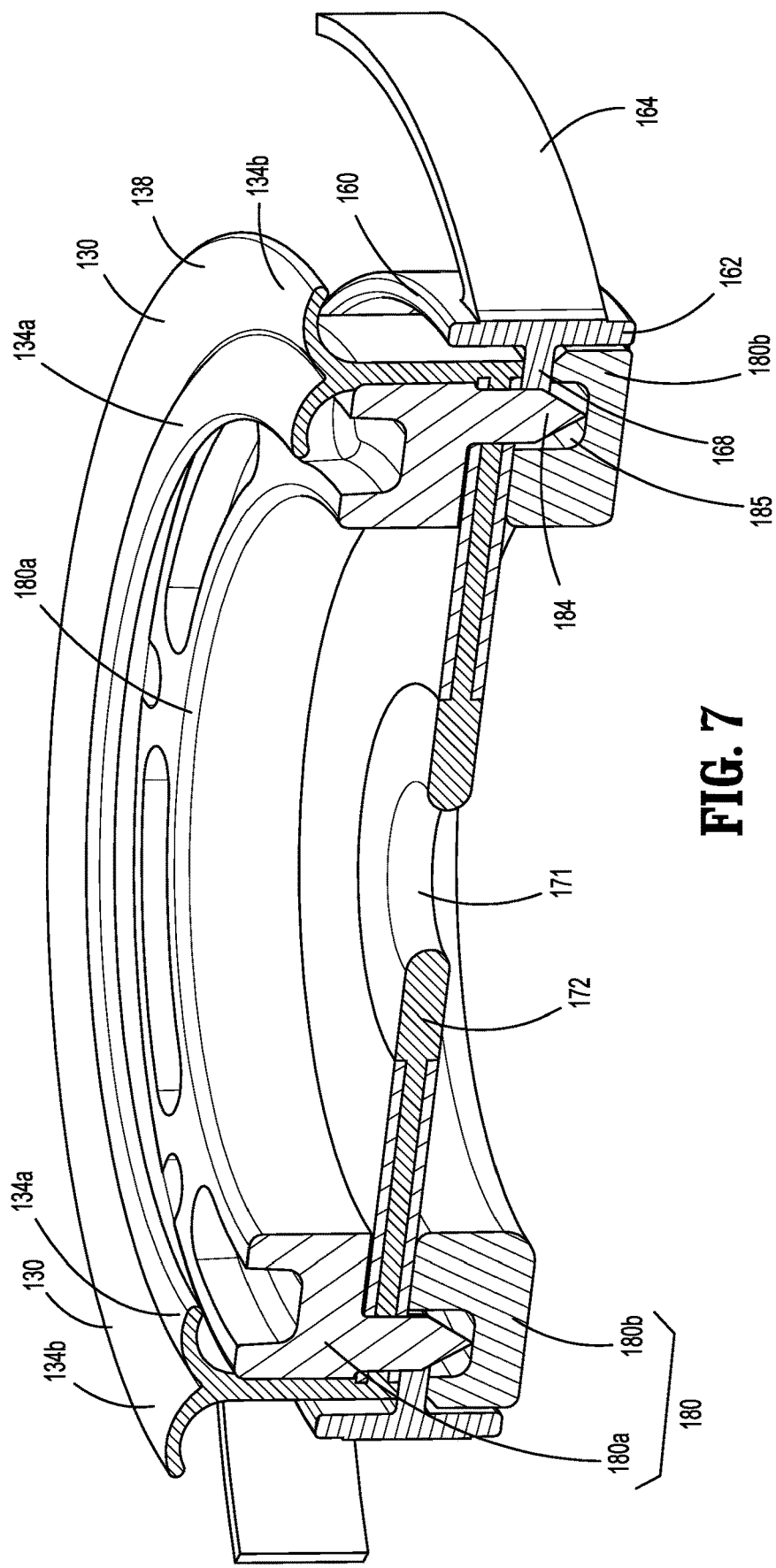
FIG. 7 is a partial perspective view of the seal assembly of FIG. 3 taken along section line 7-7 of FIG. 3.
Figure 8:
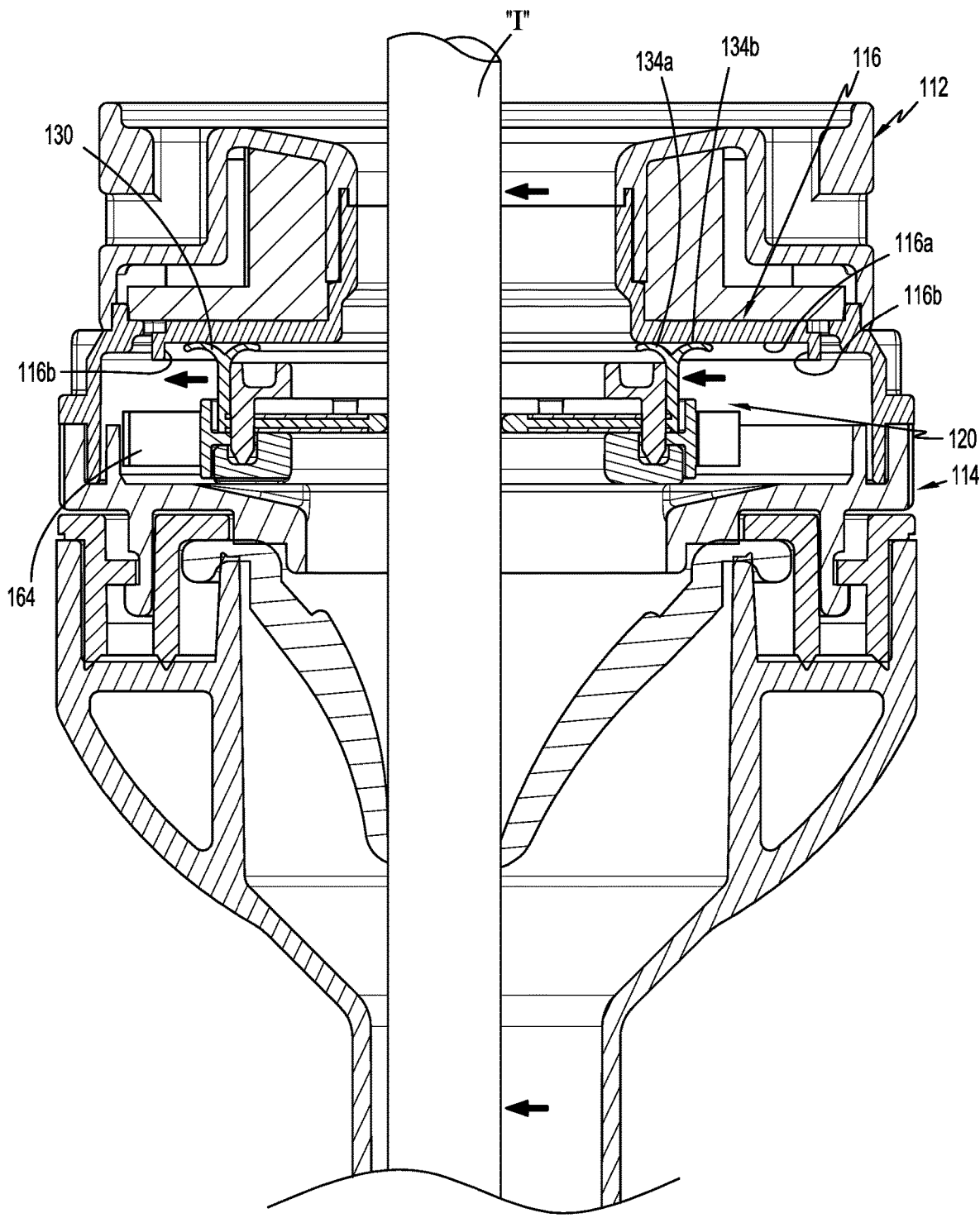
FIG. 8 is a side cross-sectional view of the proximal region of the surgical access assembly of FIG. 2, illustrating lateral movement of the seal assembly during lateral movement of a surgical instrument.

With reference to FIGS. 7 and 8, the second arcuate portion 134b of the flange seal member 130 is configured to adjustably engage a second surface such as, e.g., a lateral surface 116b (FIG. 2), of the inner housing segment 116 of the instrument valve housing 110 in a sealing relation during an off-centered movement of the seal assembly 120. The lateral surface 116b may be substantially parallel to the longitudinal axis "L-L" (FIG. 2) defined by the longitudinal passage 111 (FIG. 2) of the instrument valve housing 110. Under such a configuration, the second arcuate portion 134b may sealingly engage two surfaces that are substantially orthogonal to each other. In particular, the recess 139 (FIG. 6) defined between the first and second arcuate portions 134a, 134b of the flange portion 138 enables the second arcuate portion 134b to adjustably engage the lateral surface 116b (FIG. 2), as well as the distal surface 116a, of the inner housing segment 116 of the instrument valve housing 110 in a sealing relation during movement of the seal assembly 120. Specifically, when a portion of the centering mechanism 160 is compressed against the lateral wall 115a (FIG. 2) of the cavity 115 of the instrument valve housing 110, the second arcuate portion 134b of the flange seal member 130 may deflect radially inward against the lateral surface 116b of the inner housing section 116 to maintain sealing contact with the instrument valve housing 110. Under such a configuration, the flange seal member 130 may engage the instrument valve assembly 110 at multiple locations and enhance sealing relation with the instrument valve assembly 110. In this manner, the flange seal member 130 is configured to engage at least two surfaces of the instrument valve housing 110 in a sealing relation when the centering mechanism 160 is radially off-center, as will be discussed below.

With reference back to FIG. 4, the centering mechanism 160 is configured to bias the seal assembly 120 towards a generally centered position, i.e., concentrically positioned within the cavity 115 (FIG. 2), of the instrument valve housing 110. The centering mechanism 160 permits, e.g., radial, movement of the seal assembly 120 relative to the instrument valve housing 110 when the surgical instrument "I" is received through the seal assembly 120 and manipulated by a clinician. The centering mechanism 160 returns the seal assembly 120 to a generally centered position once the surgical instrument "I" is withdrawn from the instrument valve housing 110 or the radial movement ceases. The centering mechanism 160 is configured to engage various points of the instrument valve housing 110 to bias the centering mechanism 160 to a generally centered position.

Dynamic leaks are common when a clinician manipulates, e.g., a 5 mm surgical instrument through a 15 mm port during bariatric procedures. In order to reduce and inhibit such dynamic leaks, the centering mechanism 160 is compressible when the seal assembly 120 is diametrically displaced within the cavity 115 (FIG. 3) of the instrument valve housing 110, and the centering mechanism 160 is also resilient such that when the surgical instrument "I" is removed from the instrument valve housing 110 the centering mechanism 160 returns the seal assembly 120 back to the generally centered position. In this manner, the centering mechanism 160 may reduce occurrence of a dynamic leak during manipulation of the surgical instrument "I" within the longitudinal passage 111.

In this manner, the centering mechanism 160 is compressible and resilient to bias the off-centered seal assembly 120 towards a generally centered position within the cavity 115 (FIG. 3) of the instrument valve housing 110. Under such a configuration, once the surgical instrument "I" is withdrawn from the seal assembly 120 that is in an off-centered position, the centering mechanism 160 returns the seal assembly 120 to the generally centered position. The centering mechanism has the advantage of omnidirectional, generally constant centering forces being applied to the seal assembly. The design allows for a mechanism that always or nearly always returns the seal assembly to a central position, as the centering mechanism is always centered in its natural state. The centering mechanism can be made from surgically acceptable metals or appropriate plastics. It can also be made from materials that can be sterilized for use in a reusable trocar cannula assembly.

The centering mechanism 160 includes an annular base 162 and a plurality of spokes 164 extending radially outwards from the annular base 162. The annular base 162 defines a channel 333. The channel 333 is configured to receive a plurality of pins 184 extending from a retainer ring 182 of the first frame 180a. The plurality of pins 184 of the first frame 180a may be frictionally secured within a circular groove 185 of the second frame 180b. Alternatively, the plurality of pins 184 may be secured within the circular groove 185 of the second frame 180b with adhesive, welding, mechanical fasteners, or in any other suitable manner. As described in U.S. Pat. App. Pub. No. 2015/0025477, the content of which is incorporated herein by reference in its entirety, the plurality of spokes 164 extending from the annular base 162 of the centering mechanism 160 acts as springs that bias the annular base 162 towards a centered position within the instrument valve housing 110.

With continued reference to FIG. 7, the retainer frame assembly 180 of the seal assembly 120 is configured to couple the flange seal member 130 and the centering mechanism 160 together as a single construct to form the seal assembly 120. The retainer frame member 180 includes the first and second frames 180a, 180b. The first frame 180a includes a plurality of pins 184 extending from a retainer ring 182 of the first frame 180a. The second frame 180b defines an annular groove 185 configured to receive the plurality of the pins 184 of the first frame 180a to secure first frame 180a thereto. For example, the pins 184 may be frictionally received in the annular groove 185. Alternatively, the pins 184 may be welded, glued, adhered, bonded or otherwise secured to the annular groove 185 of the second frame 180b in order to secure the first and second frames 180a, 180b together. The retainer ring 182 of the first frame 180a is received in the recess 135 (FIG. 4) of the flange seal member 130, and the centering mechanism 160 is disposed about the retainer frame assembly 180. The plurality of pins 184 further engages respective supports 168 circumferentially arranged on and extending radially inwards from the annular base 162 of the centering mechanism 160. Further, the supports 168 are interposed between the flange seal member 130 and the second frame 180b.

With reference to FIG. 8, in use, the seal assembly 120 is initially positioned generally centered in the instrument valve housing 110 in the absence of the surgical instrument "I". The spokes 164 of the centering mechanism 160 engage the corresponding lateral wall 115a (FIG. 2) of the instrument valve housing 110. At this time, the first and second arcuate portions 134a, 134b of the flange seal member 130 engage the distal surface 116a (FIG. 2) of the instrument valve housing 110 in a sealing relation. When the surgical instrument "I" is disposed within the longitudinal passage 111 without any radial forces applied to the surgical instrument "I", the seal assembly 120 may be disposed in a generally centered position as shown in FIG. 2. However, the seal assembly 120 may move within the cavity 115 during a surgical procedure. The clinician may manipulate the surgical instrument "I" such that the seal assembly 120 may be radially displaced, which, in turn, causes some of the spokes 164 of the centering mechanism 160 to be compressed (FIG. 8). At this time, the first and second arcuate portions 134a, 134b of the flange seal member 130 may engage the distal surface 116a of the instrument valve housing 110 in a sealing relation. Further compression of the spoke 164 may cause the second arcuate portion 134b to engage the lateral surface 116b of the inner housing section 116. Once the surgical instrument "I" is withdrawn from the instrument valve housing 110, the centering mechanism 160 returns the seal assembly 120 to a generally centered position (FIG. 2), while the first and second arcuate portions 134a, 134b maintain sealing relation with the distal surface 116a of the inner housing section 116.

While the present disclosure has been shown and described herein, it will be obvious to those skilled in the art that the present disclosure is provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A surgical access assembly comprising:
   an instrument valve housing defining a cavity having a first surface and a second surface extending orthogonally from the first surface; and
   a seal assembly disposed within the cavity of the instrument valve housing, the seal assembly including:
      a flange seal member including an annular member, a flange portion extending from the annular member, and a seal portion supported by the annular member and defining an opening dimensioned to receive a surgical instrument in a sealing relation, the flange portion including a first arcuate portion and a second arcuate portion, the first arcuate portion and the second arcuate portion adjustably engaging the first surface that is orthogonal to a longitudinal axis defined by the instrument valve housing, the instrument valve housing in a sealing relation irrespective of a radial position of the flange seal member with respect to the instrument valve housing, the first arcuate portion and the second arcuate portion having a parabolic profile, the second arcuate portion is configured to engage the second surface; and
      a centering mechanism for maintaining the seal assembly centered within the cavity of the instrument valve housing.

2. The surgical access assembly according to claim 1, wherein the flange seal member is integrally formed as a single construct.

3. The surgical access assembly according to claim 1, wherein the first arcuate portion extends radially inwards from the annular member.

4. The surgical access assembly according to claim 1, wherein the second arcuate portion extends radially outwards from the annular member.

5. The surgical access assembly according to claim 1, wherein the flange portion is formed of a resilient or elastic material.

6. The surgical access assembly according to claim 1, wherein a recess is defined between the first arcuate portion and the second arcuate portion.

7. The surgical access assembly according to claim 1, wherein the first arcuate portion is configured to contact the first surface and the second arcuate portion is configured to contact the second surface.

8. The surgical access assembly according to claim 1, wherein the centering mechanism includes an annular base and a plurality of spokes extending radially from the annular base.

9. The surgical access assembly according to claim 8, wherein the annular base of the centering mechanism is disposed about the annular member of the flange seal member.

10. The surgical access assembly according to claim 9, wherein the seal assembly further includes a retaining frame assembly including a first frame and a second frame securing the flange seal member and the centering mechanism to move as a single construct.

11. The surgical access assembly according to claim 10, wherein the first frame includes a plurality of pins extending through the flange seal member and into a circular groove defined in the second frame.

12. A surgical access assembly comprising:
    a cannula;
    an instrument valve housing detachably coupled to the cannula, the instrument valve housing including a first surface and a second surface extending orthogonally from the first surface; and
    a seal assembly adjustably supported within the instrument valve housing, the seal assembly including:
       a flange seal member including an annular member, a flange portion extending from the annular member, and a seal portion extending radially inward from the annular member and defining an opening dimensioned to receive a surgical instrument in a sealing relation, the flange portion spaced apart from the seal portion, the flange portion including a first arcuate portion and a second arcuate portion extending in opposite directions from the annular member to provide a seal against the instrument valve housing as the flange seal member moves relative to the instrument valve housing, the first arcuate portion configured to engage the first surface and the second arcuate portion configured to engage the second surface; and a centering mechanism configured to bias the seal assembly towards a generally centered position within the instrument valve housing.

13. The surgical access assembly according to claim 12, wherein at least a portion of the seal portion of the flange seal member is in a superposed relation with the first arcuate portion of the flange portion.

14. The surgical access assembly according to claim 12, wherein the first arcuate portion and the second arcuate portion of the flange portion are symmetric.

15. The surgical access assembly according to claim 12, wherein the first arcuate portion and the second arcuate portion define a parabolic profile.

16. The surgical access assembly according to claim 12, wherein the first arcuate portion and the second arcuate portion are configured for respective planar contacts with the instrument valve housing.

17. The surgical access assembly according to claim 12, wherein the first arcuate portion of the flange portion is configured to engage the first surface and the second arcuate portion of the flange portion is configured to engage the second surface, the first surface orthogonal to a longitudinal axis defined by the cannula.

18. The surgical access assembly according to claim 12, wherein the flange seal member is monolithically formed.

\* \* \* \* \*